US00PP12456P2

(12) United States Plant Patent
Kaskel

(10) Patent No.: US PP12,456 P2
(45) Date of Patent: Mar. 12, 2002

(54) HEMEROCALLIS PLANT NAMED 'DANCE PARTY'

(75) Inventor: Matthew Kaskel, Miami, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/563,340

(22) Filed: May 3, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Hemerocallis plant named 'Dance Party' characterized by its small pastel yellow-colored flowers which are borne on branched scapes. The flowers do not fade in warm, bright conditions and are resistant to water spotting. Plants of 'Dance Party' bloom in mid-season and repeatedly throughout the growing season. Plants of 'Dance Party' are evergreen and highly branched, thus, they are attractive in landscapes. The plant grows vigorously and propagates easily by division or tissue culture.

2 Drawing Sheets

BACKGROUND OF THE INVENTION

The present invention comprises a new and distinct cultivar of Hemerocallis plant, hereinafter referred to by the cultivar name 'Dance Party'. The genus Hemerocallis is a member of the family Liliaceae.

Hemerocallis comprises a genus of approximately 15 species of clump-forming, herbaceous perennials which are native to central Europe, China, and particularly, Japan. The flowers of Hemerocallis are lily-like and are borne in succession atop tall, frequently-branched scapes. Individual flowers last one day; thus, Hemerocallis is commonly know as 'Daylily' in commercial trade.

In recent years, Hemerocallis has been extensively hybridized, and many cultivars exist. Hemerocallis hybrids are hardy spring- and summer-blooming plants which are particularly well-adapted to landscape plantings.

The plants form clumps of fan-shaped crowns of vertically-ranked, keeled, strap-like leaves. Plants (individual crowns) range in size from approximately 20 cm to over 90 cm in spread. Depending upon the parentage, Hemerocallis hybrids may be deciduous, evergreen or semi-evergreen.

Hemerocallis hybrids come in a range of colors including orange, yellow, pink, reddish or purplish. The flowers are funnel-shaped or campanulate with six segments joined at the base into a tube.

Asexual propagation of Hemerocallis is frequently done by division. Propagation can also be done through the use of tissue culture practices.

The new cultivar 'Dance Party' is a product of a planned breeding program and was originated by the inventor, Matthew Kaskel, from a cross made during such a program in Homestead, Fla. in April of 1995. The male and female parents are proprietary Hemerocallis selections designated by number codes which are maintained by the inventor and used for breeding purposes only. The selection comprising the new variety was chosen after commencement of flowering of the progeny in April of 1996.

Asexual reproduction of the new cultivar by tissue culture and division was performed by the inventor in Homestead, Fla. and has demonstrated that the combination of characteristics as herein disclosed for the new cultivar 'Dance Party' are firmly fixed and are retained through successive generations of asexual reproduction.

BRIEF DESCRIPTION OF THE INVENTION

The following traits have been repeatedly observed and are determined to be basic characteristics of 'Dance Party' which in combination distinguish this Hemerocallis as a new and distinct cultivar:

1. Flowers are relatively small, pastel yellow in color and thick-textured;

2. Flowers do not fade in warm, bright conditions and are resistant to water spotting;

3. Individual scapes are short and branched with many buds which open in succession for approximately 4 weeks;

4. Spent flowers shrivel, become inconspicuous, drop from the scape quickly, and do not interfere with the opening of subsequent flowers;

5. Plants begin blooming mid-season (May-June) and rebloom throughout a 90-day blooming season;

6. plants grow vigorously and propagate rapidly by division an tissue culture; and 7. plants have dark-green, evergreen foliage and a clumping habit making them attractive in landscapes even when not in bloom.

'Dance Party' has not been observed under all possible environmental conditions. The phenotype of the new cultivar may vary significantly with variations in environment such as temperature, light intensity, daylength and humidity, without any change in genotype.

BRIEF DESCRIPTION OF THE DRAWING

The accompanying color photographic illustrations show typical characteristics of Hemerocallis 'Dance Party', with colors being as nearly true as possible with illustrations of this type.

The first drawing shows a 10-month-old plant of 'Dance Party' grown from tissue culture and flowering in a landscape setting.

The second drawing is a close-up view showing the characteristics of the flowers and scape.

DETAILED BOTANICAL DESCRIPTION

The following observations, measurements and values describe plants grown in Sebring, Fla., under landscape conditions which closely approximate those generally used in horticultural practice. Color references are made to The Royal Horticultural Society (R.H.S.) Colour Chart, except where general color terms of ordinary significance are used.

Classification:

*Commercial.*—Hemerocallis cv. 'Dance Party'.

Parentage:

*Male parent.*—Proprietary selection of Hemerocallis.

*Female parent.*—Proprietary selection of Hemerocallis.

Propagation: Vegetative, by tissue culture or division.

Plant:

*Form/growth habit.*—Clump-forming; fan-shaped crowns of vertically ranked, opposite, smooth, keeled, ligulate leaves.

*Height.*—Approximately 50 cm to 55 cm including inflorescence.

*Width.*—Approximately 70 cm to 85 cm.

Foliage:

*Size.*—Mature leaves are approximately 50 cm to 60 cm long and 1.5 cm wide.

*Shape.*—The leaf blade is ligulate with an acute tip. The margins are entire. The leaves are curved over their length. The leaf is keeled and arched downward.

*Surface texture.*—The leaf blade is relatively thin with a smooth to shiny surface.

*Color.*—Upper and lower surfaces are medium-green, RHS 137A–B.

*Average number.*—Approximately 6 pairs.

*Dormancy.*—Plants are evergreen and require no dormant period. If grown in appropriate conditions, plants are capable of growing year-round.

Inflorescence:

*Borne.*—Flowers are borne in succession with new buds opening daily atop a 2- to 4-branched scape. Scapes may produce approximately 8–10 buds with each branch having 2–3 buds.

*Shape.*—Terminal, alternately-branched scape.

*Buds.*—Dimensions: Approximately 6.2 cm long and 1.8 cm wide. Color: Basically green, becoming yellower than, but closest to, RHS 150C before opening.

*Individual flowers.*—Number of sepals: three. Number of petals: three. Dimension: The diameter of the flower is approximately 8.2 cm to 9.0 cm. The sepals are approximately 5.4 cm long and approximately 3.1 cm wide. The petals are approximately 6.0 cm long and approximately 4.9 cm wide. Shape: Funnel-form to campanulate, segments ovate and moderately reflexed. Petals distincly wavy along the margins. Sepals slightly wavy along the margins. Color: Upper Surface: Sepals and petals are yellow, RHS 10A; throat is lighter than, but closest to, green RHS 144B. Lower surface: Sepals and petals are yellow, RHS 10A–B; throat is lighter than, but closest to, green, RHS 144B; sepals are tipped with RHS 146D. Texture: Moderately thick; leathery. Quantity: Approximately 8–10 flowers/buds present depending on the size of the plant and inflorescence. Branch spikes contain approximately 2 to 3 flowers/buds.

*Senescent flower.*—Spent flowers collapse and shrivel, becoming inconspicuous and eventually falling from the scape in 1 or 2 days.

*Scape.*—Approximately 45 cm to 50 cm in height and 1 cm in diameter measured at the midpoint, RHS 146A–B.

*Bracts.*—Small leaf-like bracts are present at the junctions of the branches and the scape and of the flower buds and the scape. The bracts are variable in size, approximately 1.5 cm to 3.0 cm long, RHS 146A–B.

*Time of blooming.*—In nature plants, flowering begins approximately mid-season (May–June as observed in Sebring, Fla).

*Duration of blooms.*—Individual flowers last 1 day, and the total duration of flowering is about 90 days with subsequent scapes appearing throughout the growing season.

*Fragrance.*—Slight.

Reproductive organs:

*Ovary.*—Superior, oblong, 5 mm long and 5 mm wide, RHS 146B.

*Pistil.*—8 cm long and 2.0 mm wide, RHS 14C.

*Stamens.*—Six present; filament is flat and curved, approximately 3.3 cm long and 2 mm wide, RHS 12B.

*Anthers.*—6 mm long, black to brown in color.

*Pollen.*—RHS 17A–B.

Fruit: 3-valved, loculicidal capsule 2 cm wide, 2.5 cm long, color RHS 146B to RHS 146C becoming tinged with yellow RHS 19D when ripe. Each chamber contains approximately 3–6 shiny black seeds color closest to RHS 200A, 4 to 5 mm long. Mostly round but sometimes oblong, variably shaped seeds.

Seed characteristics: Capable of producing viable seed.

Roots: Very thick, fleshy white roots with fine laterals.

Cultural:

*USDA Zone.*—Grows and blooms best when grown in USDA Zones 6 to 11.

Disease/pests: No unusual susceptibilities. Aphids may infest plants during the winter months.

I claim:

1. A new and distinct cultivar of Hemerocallis plant named 'Dance Party' as illustrated and described.

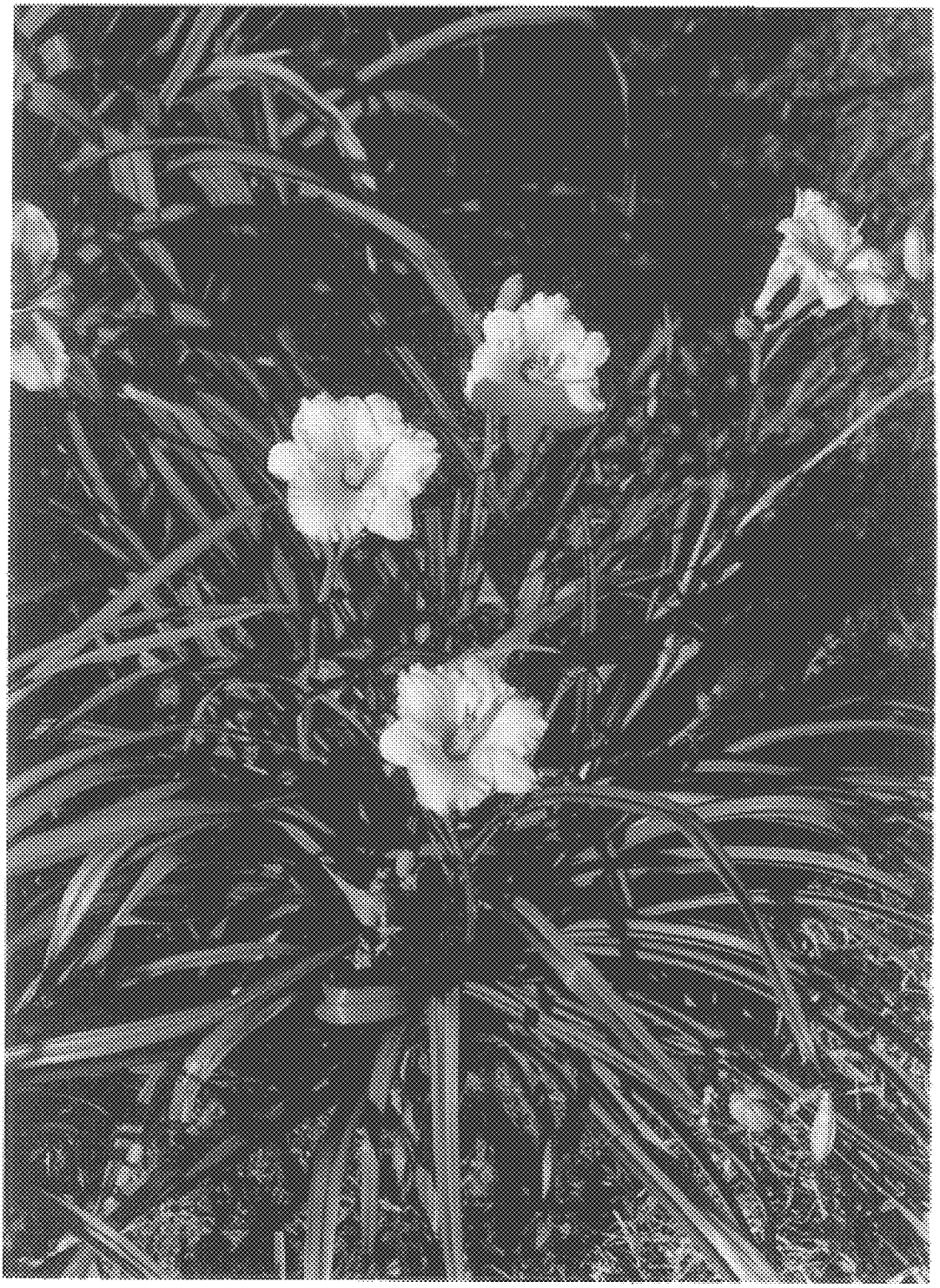

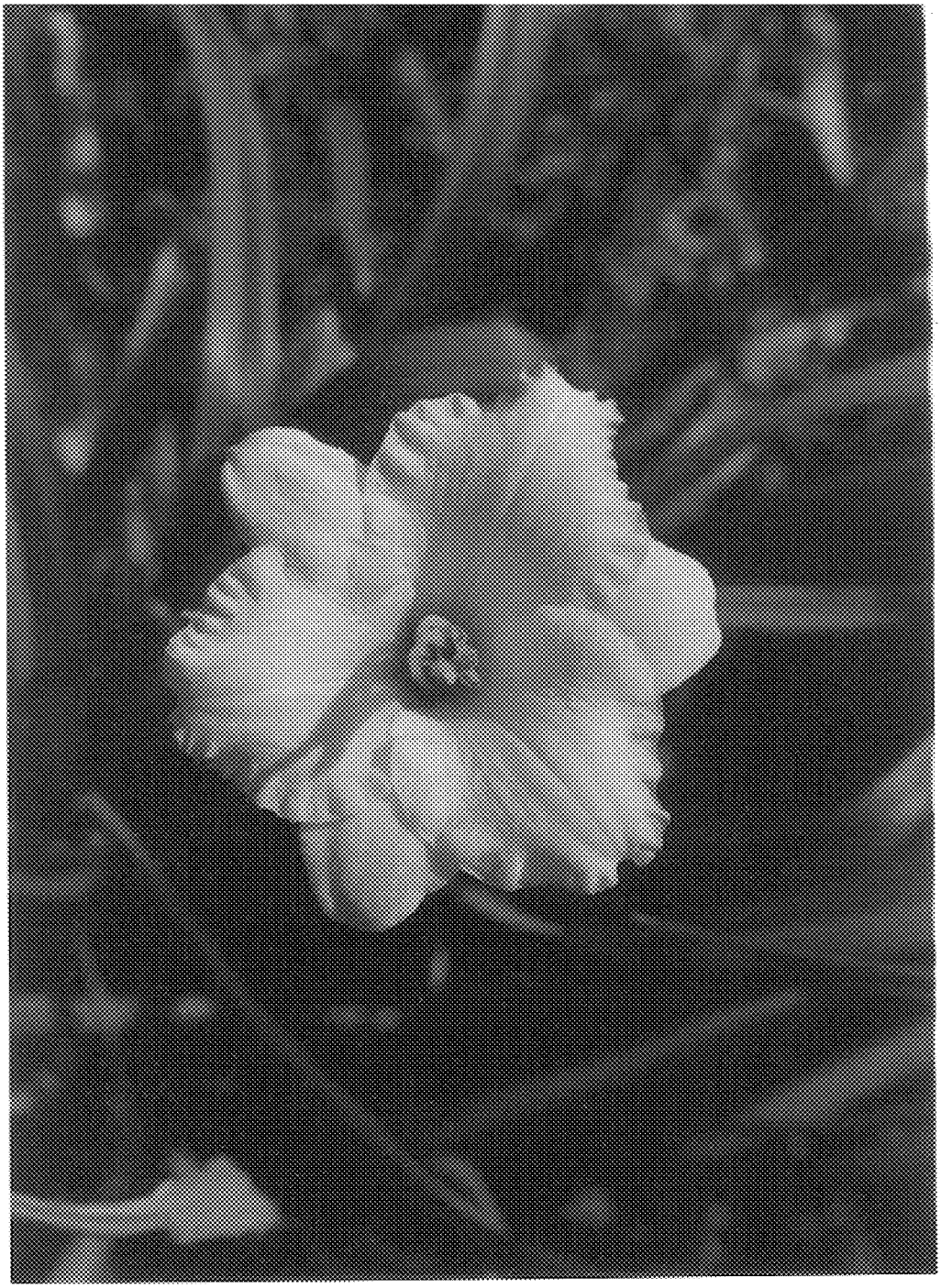

* * * * *